United States Patent [19]

Oldendorf

[11] 4,104,519

[45] Aug. 1, 1978

[54] METHOD AND APPARATUS FOR RETRIEVAL OF EXPOSURE INFORMATION FROM FILM IMAGES

[76] Inventor: William Henry Oldendorf, 2805 Angelo Dr., Los Angeles, Calif. 90024

[21] Appl. No.: 734,300

[22] Filed: Oct. 20, 1976

[51] Int. Cl.² .......................................... G01N 23/20
[52] U.S. Cl. ............................ 250/274; 250/416 TV; 358/111
[58] Field of Search ............... 250/272, 273, 274, 395, 250/416 TV, 510; 356/203; 358/111

[56] References Cited

U.S. PATENT DOCUMENTS 3,006,238  10/1961  Eberline ............................. 356/203

FOREIGN PATENT DOCUMENTS 1,016,906  1/1966  United Kingdom.

OTHER PUBLICATIONS

Moore, J. E. et al., "Automatic Direct-Reading X-Ray Spectrometry Application to Determinations of Silver," *Analytical Chemistry*, vol. 33, No. 1, Jan. 1961, pp. 61–64.
Baumgartner, W. V., "X-Ray Spectrometry Extends Film-Badge Dosimetry," *Nucleonics*, vol. 18, No. 8, Aug. 1960, pp. 76, 78 and 79.
Berman et al., "Balanced Filters for Silver Kα X Rays," *The Review of Scientific Instruments*, vol. 41, No. 6, Jun. 1970, p. 870.

*Primary Examiner*—Alfred E. Smith
*Assistant Examiner*—T. N. Grigsby
*Attorney, Agent, or Firm*—Brown & Martin

[57] ABSTRACT

A method for retrieving exposure information from film images includes selecting an exposed and developed photographic emulsion, regionally bombarding the emulsion with X-rays, regionally measuring and recording the resultant X-ray fluorescence therefrom. The method may also include the further step of translating the resultant fluorescence into a visual image. This method is carried out on suitable apparatus including a film holding device, X-ray generating device for generating an X-ray beam of a selected energy level and directing it regionally on the film, a measuring device for regionally measuring the X-rays fluorescence of the film and an image recording and/or translating device for translating the resultant fluorescence into a physical image.

26 Claims, 8 Drawing Figures

METHOD AND APPARATUS FOR RETRIEVAL OF EXPOSURE INFORMATION FROM FILM IMAGES

BACKGROUND OF THE INVENTION

The present invention relates generally to photography and pertains particularly to method and apparatus for retrieving information related to regional exposure thereby facilitating the enhancement of the image of photographic films, plates and the like.

Ordinary photography is based on the light sensitive properties of silver halides and more particularly silver bromide. In the unexposed state photographic films are made of an emulsion of silver bromide crystals and a suitable binder usually applied in a very thin layer on a suitable supporting surface such as a flexible plastic backing. The silver bromide particles are activated by exposure to light and are rendered reducable to elemental silver. The film is then developed by exposure of the film to chemical baths in a specific order. These baths are a reducing solution, a fixer, and a wash. The developing solution reduces the activated silver bromide particles to aggregates of metallic silver. These aggregates form the contrast necessary to image formation. The fixing bath washes or dissolves out of the emulsion the silver bromide which has not been reduced. The film is then dried to form what is referred to as a negative. A washing bath removes the last traces of the developer and the fixer. The silver left in the film as a result of this process forms the black and white contrast which subsequently forms the image.

Image retrieval and reconstruction commonly is accomplished by means of transillumination. This is carried out by placing the film between a light source and an observer so that the film acts as a filter. The effect is to produce regions of contrasting light and dark forming an image.

The problem with this form of image retrieval is that the relationship between the original exposure level and the resulting film opacity or ability to transmit light is very nonlinear. This is shown by for example the graph in FIG. 1 where the percent of absorption is plotted on the vertical axis against the log of exposure on the horizontal axis. Thus, from this graph it is seen that the exposure level to produce a satisfactory film is very critical. The linear range on the curve A of the graph extends between points B and C. A small variation in the exposure can result in a very large change in the percent of transmission.

It is desirable to have a linear relationship between the exposure level and the percent of transmission for ease of contrast control and for eventual image fidelity during development. Ideally, this relationship between the exposure level and percent transmission is linear throughout the entire exposure range. However, conventional transillumination techniques result in a relationship that is less than linear because superimposed silver grains obscure other silver grains aligned with them particularly in heavily exposed regions. In underexposed regions the solid angle subtended by the few silver grains results in undetectably low opacity.

For these reasons, todays photographic equipment is very complex because exposure must be precise. This equipment must function within the confines of the curve of the linear portion of the graph of FIG. 1 and can only extend the usable range incrementally outward along this predetermined curve.

Accordingly, it is desirable that a photo-processing method exists for extending the useful range of the curve of FIG. 1. More specifically, such a processing method would provide a more linear relationship between the percent transmission and the original exposure.

Applicant conceived and developed a technique of film image information retrieval that permits a more accurate analysis of the exposure of a film or photosensitive emulsion. Applicant's technique employs X-ray spectrometry, which is known, but which is new to photo-analysis.

The prior art uses of X-ray spectrometry is exemplified by the following U.S. patents:

U.S. Pat. No. 3,581,087 issued May 25, 1971 to Brinkerhoff.

U.S. Pat. No. 3,703,726 issued Nov. 21, 1972 to Stephenson.

The following articles are also of interest:

"X-ray Spectrometry Extends Film-Badge Dosimetry" by W. V. Baumgartner in the Aug, 1960 issue of NUCLEONICS, Vol. 18.

"Automatic Direct-Reading X-ray Spectrometry" by J. E. Moore, G. P. Happ and D. W. Stewart, Volume 33, No. 1, of the January, 1961 issue of the *Analytical Chemistry*.

The first article above discloses a technique for extending the over exposure range of radiation safety film badges by utilizing the ability of silver X-ray fluorescence to quantatively extend to very high radiation levels, the range from whch useful measurements can be made from radiation badge emulsions. The second article discloses a technique wherein silver X-ray fluorescences is used in quality control to measure the uniformity of silver emulsion deposited during the film manufacturing process.

These prior art methods, however, fail to recognize the applicant's problem or his solution to that problem. Neither technique recognizes the use of X-ray fluorescence as means of retrieving exposure information from silver emulsion images. Furthermore, neither technique considers the range of exposures from background fog level to maximum possible exposure level in relation to transmission radiology.

SUMMARY AND OBJECTS OF THE INVENTION

Accordingly, it is the primary object of this present invention to provide a method of overcoming the above problems of the prior art.

Another object of the present invention is to provide a method of photograph image enhancement which provides a more linear relationship between the resultant image and exposure level than prior known methods.

A further object of the present invention is to provide a method of photographic image enhancement that ovecomes the difficulties and limitations inherent in transillumination image retrieval methods.

A still further object of the present invention is provision of method and apparatus for image enhancement of photographs which employs X-ray fluorescence techniques.

In accordance with the primary aspect of the present invention, exposure information relating to the image of a metallic base photographic emulsion which has been exposed and developed is obtained by regionally bombarding the emulsion and recording the characteristic X-ray fluorescence therefrom. This information is recorded for later use by translating the resulting fluorescence into a visual image.

BRIEF DESCRIPTION OF THE DRAWING

The above and other objects and advantages of the present invention will become apparent from the following description when read in conjunction with the accompanying drawings wherein.

DETAILED DESCRIPTION OF THE PREFERRED EMBODIMENT

The present invention provides a method and system for film image enhancement and is based on the use of the phenomenon known as K-shell photoelectric absorption, or the K-edge. This refers to the designation applied to a characteristic "Break" in an X-ray absorption curve for a given element. Since the photosensitive elements of most films are silver which is most widely used currently, and mercury which was used in the early days of photography, these are the metals with which we are concerned. In considering silver, the K-shell electrons of the silver atoms orbit at an energy level of 25.5 Kev. These K-shell electrons, when bombarded with X-rays with an energy level higher than 25.4 Kev will tend to absorb some of the incident X-ray energy.

Figure 1:
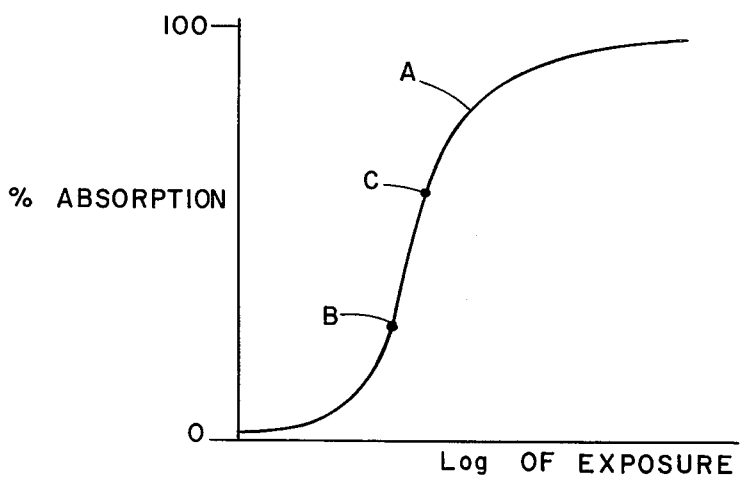
FIG. 1 is an exposure versus absorption curve for a conventional photographic emulsion.
Figure 2:
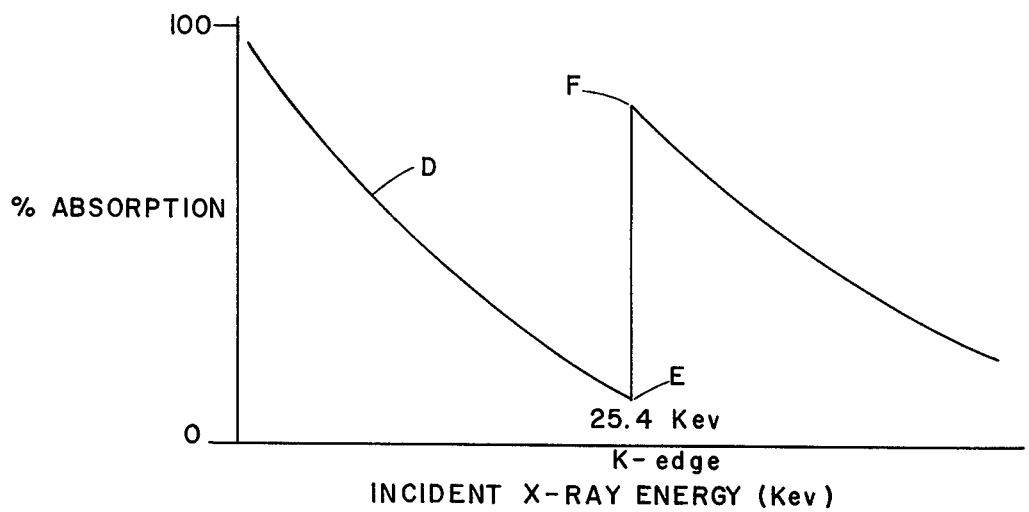
FIG. 2 is an energy absorption curve for silver.

The curve D of FIG. 2 of the drawing illustrates this absorption wherein the percentage of absorption is plotted on the vertical axis against the incident X-ray energy along the horizontal axis. A characteristic break or discontinuity in curve D occurs at 25.4 Kev, point E.

Figure 3:
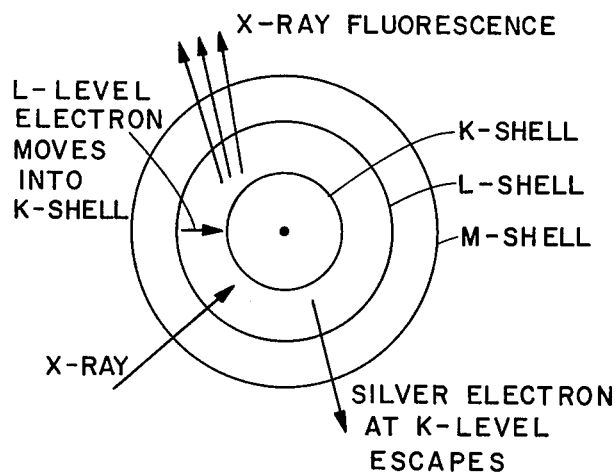
FIG. 3 is a diagrammatic illustration of X-ray fluorescence of a silver atom.

The K-shell electron can absorb a limited amount of energy. When this amount of energy is absorbed a K-shell electron becomes capable of vacating the K-shell orbit. When this occurs, usually an electron from the next higher energy shell, the L-shell, moves in to take its place as illustrated in FIG. 3. An L-shell electron exists at a higher energy level than a K-shell electron. Thus, in order for the K-shell orbital to accommodate an electron from the higher energy shell, a net loss of energy must occur during the L-shell to K-shell transfer. This energy loss is accomplished through the mechanism of X-ray emission. Occasionally the K-shell electron vacancy is filled by an electron from the M-shell.

The generation of X-rays during the transfer of an electron from one shell to another is termed X-ray fluorescence. Such X-rays produced by filling of a K-shell vacancies from the L-shell are called K-alpha X-rays and fillings from the M-shell are called K-beta rays.

Figure 4:
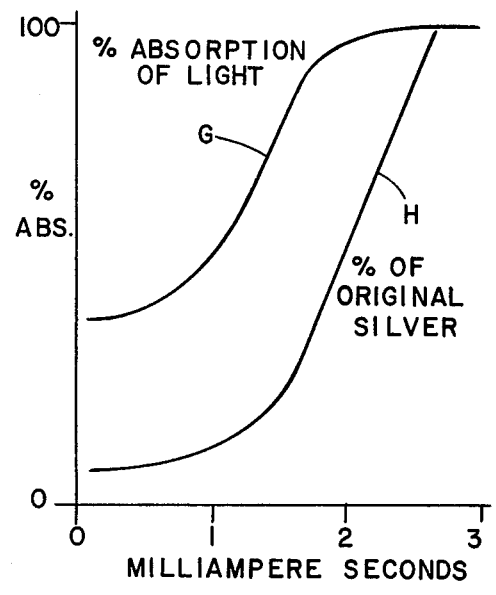
FIG. 4 illustrates graphically the relationship between light absorption and exposure for original silver content.

Utilizing X-ray fluorescence as described above instead of the traditional transillumination it is possible to show that a relatively linear relationship exists between 1) regional silver content in exposed, developed film, and 2) the amount of initial exposure of the developed film to either visible light, high energy photons or other ionizing radiation. This relationship is clearly illustrated in the graph of FIG. 4. In this graph the percent of absorption is plotted along a vertical axis as against the X-ray exposure in milli-ampere seconds along the horizontal axis. The curve of % light absorption is identified by the reference letter G while the percent of original silver is identified by the reference letter H.

In accordance with the present invention a reconstruction of a modified reproduction of an original image is carried out by the examination or a number of discrete regions on a developed emulsion or by a continuous scan of an entire image by a narrow beam of incident X-rays. The emulsion under examination by this fluorescent technique may be (1) a silver emulsion image such as a radiogram (2) a photographic transparency or (3) a silver emulsion print on an opaque paper backing, such as a photographic print.

Figure 5:
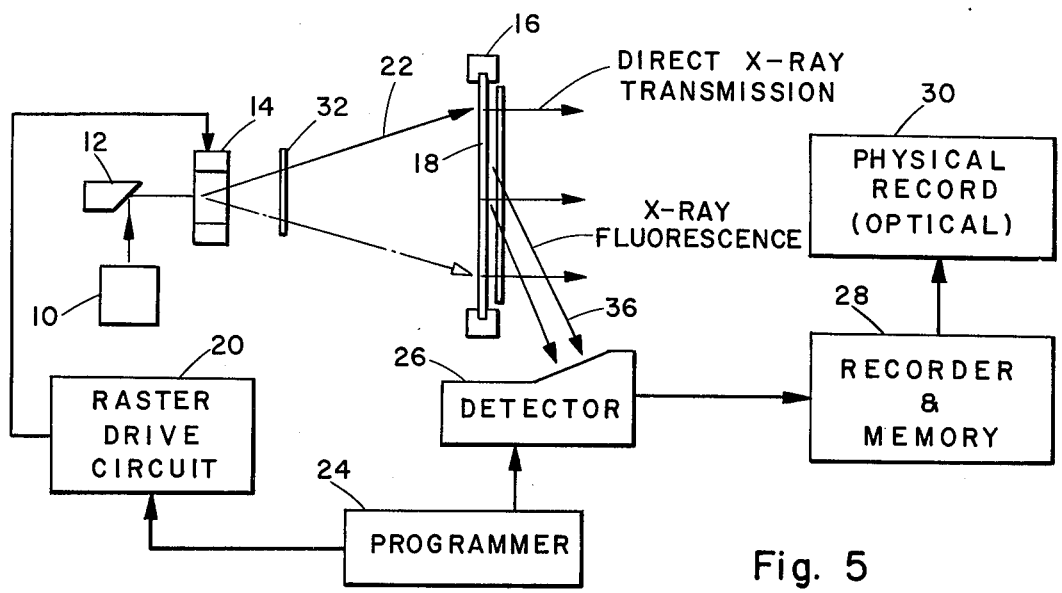
FIG. 5 is a schematic illustration of a system in accordance with the present invention.

Turning now to FIG. 5 of the drawing there is illustrated a schematic diagram of the process and the apparatus of the present invention.

The apparatus comprises a suitable X-ray source designated generally by the numeral 10 which comprises an X-ray generating machine having means for generating X-rays having characteristic energies by bombarding a suitable target such as a tungsten target 12. The machine is preferably provided with suitable collimator and beam deflecting means 14 of the usual form, for forming a narrow beam of X-ray and for deflecting the beam for scanning a film. One example of a suitable generating machine is sold under the name of Faxatron, Model 804.

The machine preferably includes suitable film holding or mounting means 16 for mounting a target 18 of selected film or other photographic emulsion.

The X-ray source includes a suitable raster drive means 20 for controlling an X-ray beam 22 for raster scanning the film. A suitable programmer 24 is tied in with the raster drive circuit for controlling the scan. The programmer is also connected to a suitable detector and analyzer 26.

The detector 26 may be of any suitable form but as an example a sodium iodide photomultiplier such as that sold under the trade name of Packard — Serial 18699. The sodium iodide detector is 1 mm by 2 inches in diameter. An electronic counter pulse height analyzer such as that sold under the trade name or mark of Packard Model 900 analyzer may also be used in or as the analyzer.

The system also includes suitable recording means 28 for recording the fluorescent count regionally from the film 18. The data received may also be produced or recorded in the form of a physical record 30. The physical record may be any suitable means such as for example another film.

An X-ray energy spectrum will usually have a broad distribution of energy range. Such a broad spectrum results in only a fraction of the X-rays being absorbed by the K-edge absorption. Ideally in order for additional photoelectric absorption to take place the incident energy spectrum should ideally peak just above the K-edge absorption level. There are two possible approaches to producing such an energy spectrum. One would be to replace the tungsten target in the X-ray generator with some other element. Such an element would be one that upon bombardment with electrons or X-rays would produce an X-ray energy spectrum of X-rays just above the K-energy of silver, antimony, tellurium or iodide would be suitable elements. In the absence of such a source it is still possible to produce an acceptable energy spectrum by use of filtration.

Applicant has found that a suitable X-ray energy spectrum can be obtained by a pre-filtration shielding material, that is, a filter 32 disposed ahead of the film 16 consisting of a sheet of 0.001 inches molybdenum and a sheet of 0.006 inches of copper.

A postfilter 34 is also found to be desirable in order to improve the signal to noise ratio. The spectrum emanating from the silver grains in the target has two components, a noise component resulting from Compton scatter and a component resulting from silver fluorescence. Other refinement on the signal to noise ratio is accomplished by the post target filtration such as a filter 34. Applicant has found a suitable post filtration material to be sheet of silver foil having a thickness of 0.0015 inches. This filter alters the spectrum of rays reaching the detector 26. The detector 26 picks up predominantly fluorescent X-rays 36 from the silver. The need for the filters may be avoided by the use of a solid state detector. However, such detectors generally require cryogenic temperatures to function properly.

For a practical machine, scan time must be as brief as possible. The use of electronic counting would thus be impractical because of the scanning time required. This can be avoided by the incorporation of an integrator directly into the photomultiplier-detector tube.

The resultant output from the above detector can be handled in two different ways. First this output may be stored in a computer for future reconstruction and interpretation. Alternately it may be made or used to modulate a light beam through a mechanical linkage for exposing another piece of unexposed film. The computer storage system can also be used to direct the light beam exposure mechanism.

Figure 6:
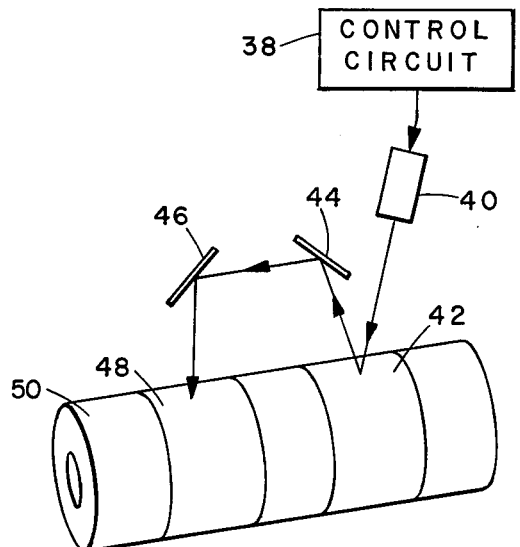
FIG. 6 is a schematic illustration of a system for exposing a new film in accordance with the present invention.

Turning now to FIG. 6, a schematic layout of a system for utilizing the data obtained above for reproducing a film for recreating a suitable image is illustrated. The apparatus comprises suitable control means 38 responsive to the recorded data which may, for example, be a computer or the like. The control means 38 is connected for controlling a light source 40 for directing a light beam, on a numerical count film 42. The apparatus functions to transfer the image in a suitable manner by way of suitable means such as mirrors 44 and 46 to a new film 48. The films 42 and 48 are mounted on a suitable device such as a rotating drum 50.

Figure 7:
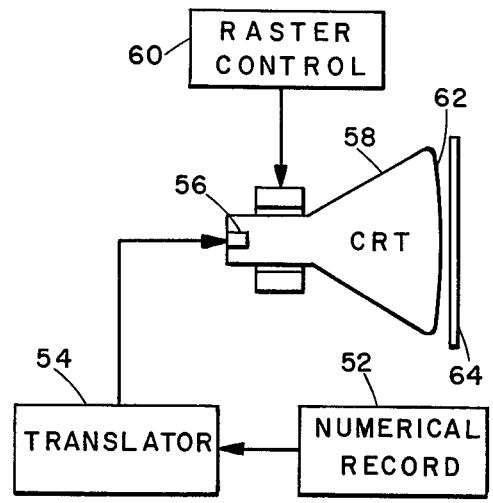
FIG. 7 is a schematic illustration of an alternate system for creating a visual image in accordance with the present invention.

Referring now to FIG. 7, there is illustrated an alternate form of apparatus for translating the fluorescent data obtained by way of the apparatus of FIG. 5 into a visual image. Such an apparatus, for example, would include suitable means for taking a numerical record such as a computer tape or memory 52, translating that by suitable translator means 54 into suitable control applied to a cathode 56 of a cathode ray tube 58 having suitable raster control means 60. The cathode ray tube then translates the data into suitable form of an image on the screen 62 of the cathode ray tube. This cathode ray tube and the image projected therewith may also be used to expose a new film 64.

Other forms of apparatus as well as modifications therein may be utilized for carrying out the present invention.

The method in carrying out the present invention consists broadly of the following steps:

First, selecting an exposed and developed metal based photographic emulsion, bombarding selected regions of the film with X-rays, measuring and recording regionally the resultant X-ray fluorescence and storing and/or translating the resultant fluorescence into a visual image. The method may also include the steps of prefilm filtration and post film filtration. Also the step of recording the resultant fluorescence may be carried out in a number of different manners such as by means of a visual record or by a suitable electronic record of some form such as a magnetic memory.

While the present invention has been specifically described with respect to silver based photographic emulsions such method may also be applied to mercury based photographic emulsions. Such mercury based emulsions were used in the early days of photography and such films and plates in existance may also be treated as discussed above for film image enhancement and/or exposure information retrieval. The K-edge energy absorption for mercury is 63.1 Kev. Accordingly the equipment and methods must be modified accordingly. This would include generating the necessary spectrum of X-ray to fall within the spectrum just above 63.1 Kev. Also, if filters were found to be necessary such filters would be such as to produce the necessary energy spectrum.

Figure 8:
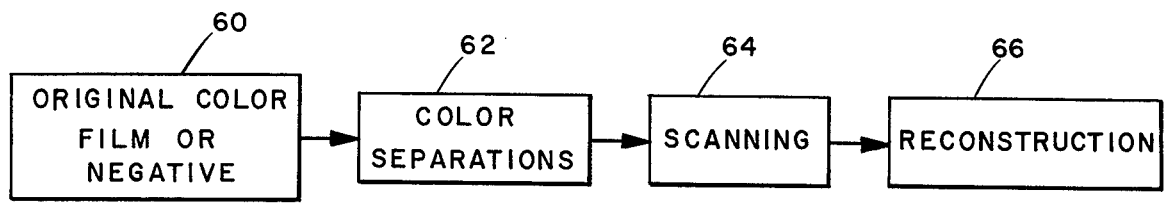
FIG. 8 is a block diagram of the method of the present invention applied to color films.

It is also contemplated that the present invention will be applied to color films. Such films are basically silver based emulsions like black and white films. The major difference however being that the silver grains of color film are pigmented whereas those of black and white are not. Accordingly, the image or exposure information may be retrieved in a manner similar to that applied to black and white film. The most efficient method of retrieval would be to use color separation of the four primary colors as a starting point. Information from each of the primary color separations would be scanned, the information gained used to reconstruct an image on another piece of primary color film and the resultant four separations put back together to produce a new picture. This method is illustrated in FIG. 8 wherein an original color film or negative 60 is taken through the steps of color separations at 62 then placed through the steps of scanning and reconstruction 64 and 66 as described above in regards to black and white film.

The present invention has numerous advantages over the normal transillumination method. For example, because of the generally linear relationship existing between the fluorescence achieved by the present method and the original exposure more information can be retrieved from regions normally considered too under or overexposed for usual interpretation. Images ordinarily obscured by fading or by non-silver containing material in the original silver emulsion image would still be retrievable. This would be of value in restoring historical or otherwise deteriorated photographic images.

An existing traditional radiograph would be suitable for a scanning measurement with storage of regional silver content in a computer matrix. The image would then be available for computer manipulation of image data in under and overexposed regions. This would allow considerable information to be retrieved from the existing film that is not now accessible from traditional transmission viewing. This would optimize radiographs for halftone printing in publications.

Distracting details which may be present in the non-silver portion of the emulsion or of the film base would not be printed in the image retrieved by fluorescent analysis. Other advantages include the transmission of two distant locations by telephone or radio where the image could be reproduced with great fidelity.

The regional bombardment and the regional measurement as used herein means a uniform areal analysis of preselected area or portion of a film. By this is meant a statistically programmed or non-random analysis as opposed to a random or unstructured analysis. In other words, the selected area must be uniformly scanned to detect and record the precise amount and location of any variation in the silver content of the film, which is related or determined by the exposure thereof. This may, for example, constitute a point-by-point analysis of each separate grain within the film if such is necessary in order to obtain the necessary resolution of the image or information thereon. At least, sufficient adjacent and uniformly spaced point are to be analyzed to at least equal the original photo clarity or resolution. As an example, a 35 mm photo would have approximately 1 million grains or points.

A fine grained film, for example, would of necessity require more points and more closely spaced points of analysis than a coarse grained film. This would ensure an accurate representation of the actual exposure of a film itself and any image formed thereon.

While the present invention has been illustrated and described by means of specific embodiments it is to be understood that numerous changes and modifications may be made therein without departing from the spirit and scope of the invention as defined in the appended claims.

Having described may invention, I now claim:

1. A method of retrieving image information from a photosensitive emulsion comprising the steps of:
   selecting a region of an exposed and developed photographic emulsion;
   systematically raster scanning the entire selected region of said emulsion with X-rays on a high density point by point basis;
   measuring regionally the resultant fluorescence; and
   recording the resultant fluorescence intensity and location.

2. The method of claim 1 including the further step of:
   translating the density of the resultant fluorescence into a visual image.

3. The method of claim 1 including the further step of translating the density of the resultant fluorescence into a number related to regional exposure.

4. The method of claim 1 wherein the step of raster scanning said film is carried out with X-rays at an energy level higher than 25.5 Kev.

5. The method of claim 1 wherein the step of raster scanning said emulsion is carried out by generating an X-ray having an energy spectrum the peaks just above the K-edge absorption level of the metallic base of the emulsion, and selectively scanning regions of said film with said X-ray.

6. A method of retrieving exposure information from a photosensitive emulsion comprising the steps of:
   selecting an exposed and developed photographic emulsion;
   bombarding regions of said emulsion with X-rays by generating an X-ray having an energy spectrum that peaks just above the K-edge absorption level of the metallic base of the emulsion, wherein the step of generating said X-rays is carried out in an X-ray generating machine by providing a target of tungsten, and filtering the resultant X-ray by means of a filter consisting of a sheet of 0.001 inches molybdenum and a sheet of 0.006 inches copper and selectively scanning regions of said film with said X-ray;
   measuring regionally the resultant fluorescence; and
   recording the resultant fluorescence.

7. The method of claim 6 including the further steps of improving the signal to noise ratio of the rays emanating from the emulsion by the step of filtering the rays therefrom prior to measuring said flourescence, and the step of filtering is carried out by filtering said rays by means of a sheet of silver having a thickness of approximately 0.0015 inches.

8. A method of retrieving exposure information from a photosensitive emulsion comprising the steps of:
   selecting an exposed and developed photographic emulsion;
   bombarding regions of said emulsion with X-rays by generating an X-ray having an energy spectrum that peaks just above the K-edge absorption level of the metallic base of the emulsion, wherein the step of generating said X-rays are carried out in an X-ray generating machine by selecting and providing a target element of antimony, and selectively scanning regions of said film with said X-ray;
   measuring regionally the resultant fluorescence; and
   recording the resultant fluorescence.

9. A method of retrieving exposure information from a photosensitive emulsion comprising the steps of:
   selecting an exposed and developed photographic emulsion;
   bombarding regions of said emulsion with X-rays by generating an X-ray having an energy spectrum that peaks just above the K-edge absorption level of the metallic base of the emulsion, wherein the step of generating said X-rays are carried out in an X-ray generating machine by selecting and providing a target element of tellurium, and selectively scanning regions of said film with said X-ray;
   measuring regionally the resultant fluorescence; and
   recording the resultant fluorescence.

10. A method of retrieving exposure information from a photosensitive emulsion comprising the steps of:
    selecting an exposed and developed photographic emulsion;
    bombarding regions of said emulsion with X-rays by generating an X-ray having an energy spectrum that peaks just above the K-edge absorption level of the metallic base of the emulsion, wherein the step of generating said X-rays are carried out in an X-ray generating machine by selecting and providing a target element of iodide and selectively scanning regions of said film with said X-ray;
    measuring regionally the resultant fluorescence; and
    recording the resultant fluorescence.

11. A film exposure information retrieval system, said system comprising:
    means for supporting a selected exposed and developed photosensitive emulsion;
    X-ray generating means for generating a beam for directing on said film;

raster drive means for deflecting the X-ray beam for selectively directing said beam on selected regions of said film;

means for regionally measuring the X-ray fluorescence of said photosensitive emulsion;

and means for recording information relating to the location and intensity of said X-ray fluorescence.

12. The exposure information retrieval system of claim 11 including means for forming a physical image that is a linear function of said fluorescence.

13. The exposure information retrieval system of claim 11 wherein said emulsion is a silver based emulsion.

14. The exposure information retrieval system of claim 11 wherein said emulsion is a mercury based emulsion.

15. The exposure information retrieval system of claim 11 wherein said emulsion is an exposed and developed color emulsion.

16. The exposure information retrieval system of claim 11 wherein said means for measuring said fluorescence comprises a crystal-photomultiplier detector.

17. The exposure information retrieval system of claim 16 wherein said photomultiplier is a sodium iodide crystal photomultiplier.

18. The exposure information retrieval system of claim 11 wherein said means for measuring said fluorescence comprises a solid-state detector.

19. The information retrieval system of claim 11, said X-ray generating means comprises means for generating X-rays having an energy level which peaks between 25.5 and 30 Kev.

20. The information retrieval system of claim 19 wherein said X-ray generating means includes a target material of antimony.

21. The information retrieval system of claim 19 wherein said X-ray generating means includes a target material of Tellurium.

22. The information retrieval system of claim 19 wherein said X-ray generating means includes a target material of iodide.

23. The information retrieval system of claim 19 wherein said X-ray generating means includes a target material of tungsten, and said system includes a filter between said generating means and said photo emulsion.

24. The information retrieval system of claim 23 wherein said filter comprises a sheet of molybdenum having a thickness of approximately 0.001 inches, and a sheet of copper having a thickness of approximately 0.006 inches.

25. The information retrieval system of claim 24 including a filter disposed between said emulsion and said detector.

26. The information retrieval system of claim 25 wherein said filter between said emulsion and said detector comprises a sheet of silver having a thickness of approximately 0.0015 inches.

* * * * *